US008950580B2

(12) United States Patent
Sharpe et al.

(10) Patent No.: US 8,950,580 B2
(45) Date of Patent: Feb. 10, 2015

(54) INTRAVENOUS FLUID HANGER HOUSING

(71) Applicants: Gary L. Sharpe, Naples, FL (US); Doug Clouser, Galloway, OH (US)

(72) Inventors: Gary L. Sharpe, Naples, FL (US); Doug Clouser, Galloway, OH (US)

(73) Assignee: Gary L. Sharpe, Naples, FL (US)

( * ) Notice: Subject to any disclaimer, the term of this patent is extended or adjusted under 35 U.S.C. 154(b) by 185 days.

(21) Appl. No.: 13/771,279

(22) Filed: Feb. 20, 2013

(65) Prior Publication Data

US 2013/0214655 A1 Aug. 22, 2013

Related U.S. Application Data

(60) Provisional application No. 61/600,768, filed on Feb. 20, 2012.

(51) Int. Cl.

| | |
|---|---|
| ***A61B 17/06*** | (2006.01) |
| ***A61B 19/02*** | (2006.01) |
| ***A61L 15/00*** | (2006.01) |
| ***A61J 1/16*** | (2006.01) |
| ***A47F 7/28*** | (2006.01) |
| *A61J 1/14* | (2006.01) |

(52) U.S. Cl.

CPC ... *A61J 1/16* (2013.01); *A47F 7/28* (2013.01); *A61J 1/1437* (2013.01)

USPC ........................................... 206/438; 206/363

(58) Field of Classification Search

USPC .......... 206/363, 528, 530, 571; 190/100, 109; 312/209, 215, 222, 326, 329; 220/475, 220/677–679, 810, 836, 843, 844; 604/29, 604/6.15, 317, 319

See application file for complete search history.

(56) References Cited

U.S. PATENT DOCUMENTS 4,433,244 A * 2/1984 Hogan ..................... 250/455.11
D623,398 S * 9/2010 Meiser et al. ............... D3/203.1
2004/0217036 A1* 11/2004 Ginsberg et al. ........... 206/524.7
2013/0081966 A1 4/2013 DeVore

* cited by examiner

*Primary Examiner* — Luan K Bui
*Assistant Examiner* — Rafael Ortiz
(74) *Attorney, Agent, or Firm* — Standley Law Group LLP

(57) ABSTRACT

A housing secures an intravenous fluid bag along a portion of a support pole. The intravenous bag is suspended inside the housing, which is formed from three molded parts. A molded back part and a molded end part are joined in a permanent manner along a seam line, and these molded parts define a majority of the housing. A molded door part completes the housing, the molded door part being hingedly attached to the molded back part, providing the housing with an open and a closed position. Aligned slots in the molded end part allow the support pole portion to pass through the housing interior when the housing is in the closed position, and at least one cradle, attached to the molded end part, secures the support pole portion. The molded door part can be latched when in the closed position.

17 Claims, 1 Drawing Sheet

INTRAVENOUS FLUID HANGER HOUSING

CROSS-REFERENCE TO RELATED APPLICATIONS

This application is a non-provisional of U.S. 61/600,768, filed on 20 Feb. 2012, which is incorporated by reference as if fully recited herein and to which a claim of priority is made.

TECHNICAL FIELD

The disclosed embodiments of the present invention relate to a housing for providing a secure and private system for delivering fluids intravenously to a patient in a medical setting.

BACKGROUND

The delivery of fluids to a patient intravenously is known in the art, especially in applications where the patient is being transported. In such applications, the bag from which the fluids are being dispensed is suspended from a support pole, the difference between its height and the position of the patient providing the requisite gravity flow.

For a number of reasons, including patient security and protection of patient medical information, it is becoming increasingly important to provide something more than a simple bag of the fluid hanging from a support pole.

It is therefore an unmet advantage of the prior art to provide an intravenous fluid hanger assembly that is reliably transported and provides the necessary amount of privacy and security.

SUMMARY

This and other unmet advantages are provided by a housing for securing an intravenous fluid bag along a support pole. Such a housing is formed from three molded parts. A molded back part and a molded end part are joined in a permanent manner along a seam line. A molded door part is hingedly attached to the molded back part along an edge of the respective parts, providing the housing with an open and a closed position and a hollow interior.

A set of aligned slots, formed in the molded end part, are sized and adapted to allow a portion of the support pole to pass through the housing from a top to a bottom thereof when the housing is in the closed position. This portion of the support pole is secured to a mounting means that is attached to the molded end part, inside the housing.

A means for latching the molded door part to the molded end part when the housing is in the closed position is located on the respective parts, as is a means for mounting the intravenous fluid bag inside the housing.

In some embodiments, the molded back part is joined to the molded end point by thermal welding.

In some embodiments, the means for hingedly attaching comprises complementary hinge components formed on each of the molded door part and the molded back part, while in some other embodiments, the means is a separately-formed hinge attached to each of the molded door part and the molded back part.

In some embodiments, each of the molded parts is formed from a high-impact thermoplastic, with a preferred high-impact thermoplastic being an acrylonitrile-butadiene-styrene (ABS) copolymer.

BRIEF DESCRIPTION

A better understanding of the disclosed embodiments will be obtained from a reading of the following detailed description and the accompanying drawings wherein identical reference characters refer to identical parts and in which.

DETAILED DESCRIPTION

Figure 1:
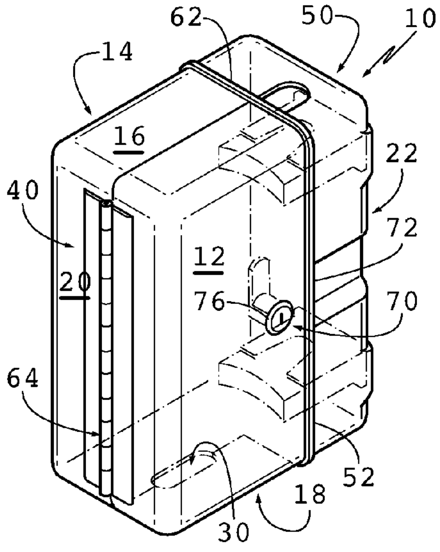
FIG. 1 is a left front perspective view of an embodiment of the housing, in a closed condition.

FIG. 1 shows a perspective view, taken from an upper left front point of view, of an embodiment 10 of an intravenous fluid hanger housing, depicted in a closed position. The embodiment 10 will commonly be used in association with a support pole (not shown), as described in more detail below.

With the embodiment 10 arranged in the closed position of FIG. 1, many features thereof are visible. The housing 10 is a generally hollow, rectanguloid body with front and rear faces 12, 14, top and bottom faces 16, 18 and left and right side faces 20, 22. In the depicted housing 10, each of the six corners at which three adjoining faces meet, as well as each of the twelve edges along which a pair of faces meet, is shown as being smoothly radiused, which provides some functional advantage as well as an improved aesthetic appearance.

In looking at the housing 10 in a slightly different way, it is observed to be formed from three molded parts 30, 40, 50. Of these, the first is a door part 30, the second is a back part 40 and the third is an end part 50. Door part 30 comprises about one-half of the area of left side face 20, about one-third of the area of top and bottom faces 16, 18 and about two-thirds of the area of front face 12. The back part 40 comprises the remaining one-half of the left side face 20, about two thirds of the rear face 14 and about one-third of the top and bottom faces 16, 18. The end part 50 comprises the remaining about one-third of the front and rear faces 12, 14, the remaining about one-third of the top and bottom faces 16, 18 and all of the right side face 22.

The three molded parts 30, 40, 50 are joined together to provide the housing with a securable interior volume. Back part 40 and end part 50 are joined in a permanent manner along a seam line 62, which may be adapted and shaped to facilitate the particular manner of joining selected, such as by a thermal welding or an adhesive bonding.

Door part 30 is joined to back part 40 in a hinged manner along the left side face 20. The hinge 64 can be formed from individual hinge parts that are integral with the respective door part 30 and back part 40, or the hinge can be separately formed and then attached to the door and back parts. Because of its particularly good properties in hinge applications, a separately-formed hinge may be preferred to be polypropylene, in which case the parts 30, 40 can be formed from another material that may have preferred properties for serving as the housing 10.

Figure 2:
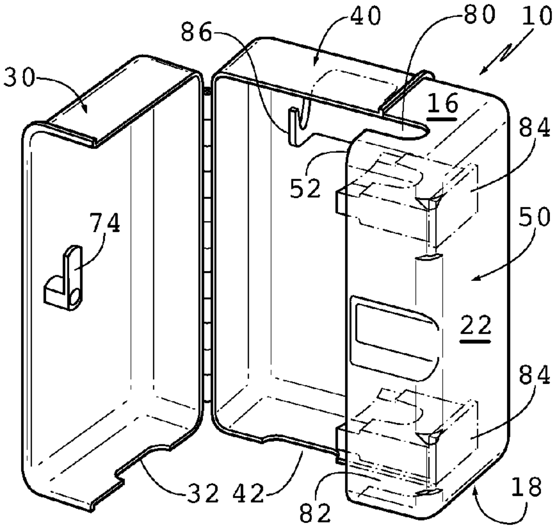
FIG. 2 is a right front perspective view of the FIG. 1 embodiment, with the housing opened to show internal features.

When in a closed position, door part 30 and end part 50 meet along an edge line 52 that would be an extension of the seam line 62 that joins back part 40 and the end part 50, but the door and end parts are only adjacent along this extension and there is no actual joining of the parts. A latch means 70, preferably a keyed latch means, is provided on the door part 30 and engages a slot 72 on the back part 40. In FIG. 2, a cam 74 is shown, shaped and adapted to be received in the slot 72. Cam 74 is rotated by a lock 76 on the outside of door 30.

FIG. 2 further depicts the housing 10, but in an opened condition to show features of the interior. In combination with FIG. 1, it shows many features of the housing 10. A notable feature FIG. 2 is an open-ended slot 80 on the top face 16 that extends from the edge line 52 towards the right side face 22. A corresponding open-ended slot 82 is provided directly below on the bottom face 18. These aligned slots 80, 82 provide a channel through which an IV pole can be positioned when the door part 30 is open (as in FIG. 2), but the closing of the door part (as in FIG. 1) closes off the open end of the slots, effectively securing the IV pole.

One or more cradles 84 for the IV pole allow the IV pole to be directly secured. FIG. 2 shows two such cradles 84 being employed. As depicted, the cradles 84 are fixed in place on an interior wall of the end part 50.

A further pair of slots, these being corresponding and facing slots 32, 42 on the bottom face 18 of door part 30 and back part 40 allow tubing from a IV bag being retained in the housing to exit from through the bottom face.

FIG. 2 also shows a means 86 for hanging an IV bag inside the housing 10. Typically, this means for hanging will be similar to that used on a conventional IV pole and can be a hook, hanger or the like. Because the IV bag is suspended from the housing 10 and not directly from the pole, the housing itself may be moved along the pole while in use, although this does require opening the housing 10.

Figure 3:
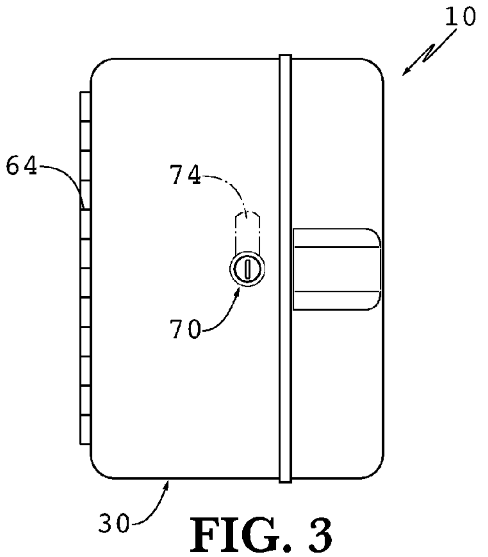
FIG. 3 is a front elevation view of the FIG. 1 embodiment, with the housing closed.

FIG. 3 is a front elevation view of the housing 10, showing the door part 30 in a closed position, and with cam 74 of the lock means 70 in the unlocked position.

Figure 4:
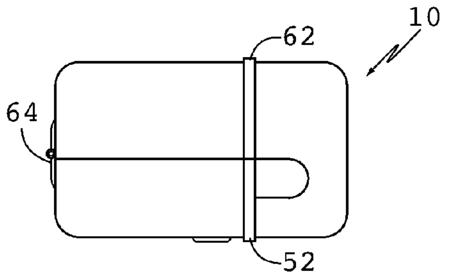
FIG. 4 is a top plan view of the FIG. 1 embodiment, with the housing closed.

FIG. 4 is a top plan view of the housing 10.

Figure 5:
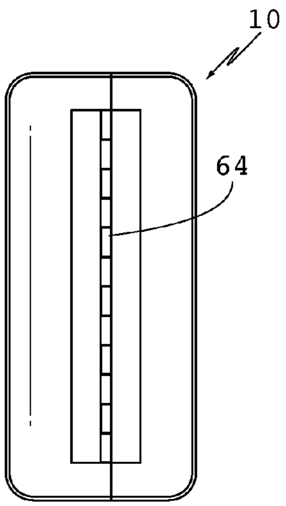
FIG. 5 is a left side elevation view of the FIG. 1 embodiment, with the housing closed.

FIG. 5 is a left side elevation view of the housing 10.

Many materials will be known as useful for the housing 30. As molding, and especially injection molding, is an effective manner of forming devices such as this, thermoplastic materials that are suitable for injection molding will be preferred. Other aspects of the design decision as to material will be influenced by further considerations, such as the desired amount of impact resistance (acrylonitrile-butadiene-styrene copolymers providing exemplary impact resistance), the desired flexibility of a molded hinge (polypropylene providing an exemplary flexibility) or the desired amount of transparency/opacity of the material (wide amount of materials useful). In addition to the thermoplastics, drawn and/or pressed metal sheets would also be useful for forming the housing.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A housing for securing an intravenous fluid bag along a support pole, comprising:

a molded door part;

a molded back part;

a molded end part, joined to the molded back part along a seam line;

means for hingedly attaching the molded door part to the molded back part along a edge of the respective parts, providing the housing with an open and a closed position;

aligned slots, formed in the molded end part, sized and adapted for a portion of the support pole to pass through the housing when the housing is in the closed position;

means for securing the portion of the support pole, mounted inside the housing in the molded end part;

means for latching the molded door part to the molded end part when the housing is in the closed position; and means for mounting the intravenous fluid bag inside the housing.

2. The housing of claim 1, wherein:

the molded back part is joined to the molded end point by thermal welding.

3. The housing of claim 2, wherein:

the means for hingedly attaching comprises complementary hinge components formed on each of the molded door part and the molded back part.

4. The housing of claim 3, wherein:

each of the molded parts is formed from a high-impact thermoplastic.

5. The housing of claim 4, wherein:

the high-impact thermoplastic is an acrylonitrile-butadiene-styrene (ABS) copolymer.

6. The housing of claim 2, wherein:

the means for latching further comprises a lock.

7. The housing of claim 2, wherein:

the means for hingedly attaching comprises a separately-formed hinge attached to each of the molded door part and the molded back part.

8. The housing of claim 7, wherein:

each of the molded parts are formed from a high-impact thermoplastic.

9. The housing of claim 8, wherein:

the high-impact thermoplastic is an acrylonitrile-butadiene-styrene (ABS) copolymer.

10. The housing of claim 1, wherein:

the means for hingedly attaching comprises complementary hinge components formed on each of the molded door part and the molded back part.

11. The housing of claim 10, wherein:

each of the molded parts is formed from a high-impact thermoplastic.

12. The housing of claim 11, wherein:

the high-impact thermoplastic is an acrylonitrile-butadiene-styrene (ABS) copolymer.

13. The housing of claim 10, wherein:

the means for latching further comprises a lock.

14. The housing of claim 1, wherein:

the means for hingedly attaching comprises a separately-formed hinge attached to each of the molded door part and the molded back part.

15. The housing of claim 14, wherein:

each of the molded parts are formed from a high-impact thermoplastic.

16. The housing of claim 15, wherein:

the high-impact thermoplastic is an acrylonitrile-butadiene-styrene (ABS) copolymer.

17. The housing of claim 14, wherein:

the means for latching further comprises a lock.

* * * * *